United States Patent

Heagle et al.

[11] Patent Number: 5,190,657
[45] Date of Patent: Mar. 2, 1993

[54] BLOOD FILTER AND METHOD OF FILTRATION

[75] Inventors: David G. Heagle, Toutman; John J. Hiers, Elkin, both of N.C.

[73] Assignee: Lydall, Inc., Manchester, Conn.

[21] Appl. No.: 733,613

[22] Filed: Jul. 22, 1991

[51] Int. Cl.$^5$ ............ B01D 37/00; B01D 39/04; B01D 39/06; B01D 39/08
[52] U.S. Cl. .................. 210/645; 210/490; 210/500.36; 210/505; 210/508; 210/509; 210/767; 422/101; 428/283; 428/285; 428/286; 428/287; 428/323; 428/327
[58] Field of Search ........... 210/505, 508, 509, 500.36, 210/490, 645, 651, 767; 428/283, 284, 286, 285, 287, 323, 327; 422/101

[56] References Cited

U.S. PATENT DOCUMENTS

| | | | |
|---|---|---|---|
| 3,448,041 | 6/1969 | Swank | 210/446 |
| 3,765,536 | 10/1973 | Rosenberg | 210/446 |
| 4,053,420 | 11/1977 | Marx | 210/435 |
| 4,132,650 | 1/1979 | Kirsch et al. | 210/508 |
| 4,157,976 | 6/1979 | Meyst et al. | 210/449 |
| 4,186,101 | 1/1980 | Reinhardt | 210/509 |
| 4,274,914 | 6/1981 | Keith et al. | 55/528 |
| 4,455,237 | 6/1984 | Kinsley | 210/767 |
| 4,701,267 | 10/1987 | Watanabe et al. | 210/806 |
| 4,784,892 | 11/1988 | Storey et al. | 428/283 |
| 4,813,948 | 3/1989 | Insley | 428/283 |
| 4,859,340 | 8/1989 | Hou et al. | 210/505 |
| 4,880,548 | 11/1989 | Pall et al. | 210/508 |
| 4,889,764 | 12/1989 | Chenoweth et al. | 428/283 |
| 4,904,343 | 2/1990 | Giglia et al. | 428/287 |
| 4,936,993 | 6/1990 | Nomura | 210/446 |
| 4,936,998 | 6/1990 | Nishimura et al. | 210/767 |
| 5,077,116 | 12/1991 | Lefkowitz | 428/323 |

Primary Examiner—Robert A. Dawson
Assistant Examiner—Sun Uk Kim
Attorney, Agent, or Firm—Griffin, Butler, Whisenhunt & Kurtossy

[57] ABSTRACT

A filter material for filtering leucocytes from a fraction of or whole human blood, comprises a shape-sustaining laid textile web having a thickness of between about 2 millimeters to about 12 millimeters and a bulk density of about 0.05 to 0.4 g/cm$^3$. The web has a plurality of interlocked, staple, textile fibers with average deniers between about 0.05 and 0.75 and average lengths between about 3 millimeters and 15 millimeters. The textile fibers are substantially uniformly distributed in the web so as to form a matrix of the textile fibers with spaces between adjacent interstices of interlocked fibers. A plurality of fibrillated particles of a polymeric material, e.g. a textile fiber material, having a surface area of between 5 and 60 square meters per gram are substantially disposed within the spaces of the matrix. The fibrillated particles have a plurality of fine fibrils which are interlocked with adjacent textile fibers of the spaces such that the fibrillated particles are not substantially displaced from the web during filtration of the blood. The weight ratio of the fibrillated particles to the textile fibers is between about 1:99 and 40:60.

44 Claims, 2 Drawing Sheets

BLOOD FILTER AND METHOD OF FILTRATION

The present invention relates to a filter material and a method of filtering blood fractions or whole blood and, more particularly, to such filter material and method which can, among others, filter leucocytes from a blood fraction or whole blood.

BACKGROUND OF THE INVENTION

As has been well recognized by the art for some time, it is important for some uses of blood fractions or whole blood to remove from that blood certain indigenous matter, and the art has proposed, over a number of years, many different types of filters to achieve that result. These filters may be, broadly, divided into two classes, i.e. blood sieves and blood component filters. Blood sieves are very coarse in pore size and have a strong tendency to block quickly if the pore size is finer than a minimum. Blood sieves are used, primarily, for removing large particles, e.g. debris, agglomerates and the like from blood, especially stored blood, while blood component filters are used, primarily, for removing selected natural blood components, e.g. red cells ($6-9\mu$), platelets ($2-4\mu$) and leucocytes ($6-20\mu$). The present invention relates to this latter type of device, i.e. a blood component filter, and, particularly, to such a blood filter which has the capability of substantially filtering leucocytes from the blood or blood fraction.

One of the earlier more successful blood component filters is described in Swank U.S. Pat. No. 3,448,041, issued on Jun. 3, 1969. The filter of that patent is a thick non-woven fibrous mat, usually made of polyester fibers, with pore sizes up to several hundred microns. The filter is made of fine fibers and is designed to selectively filter storage-altered components of blood used in blood transfusions, e.g. platelets and leucocytes, which become somewhat sticky and agglomerate during storage. These filters, however, have serious disadvantages in use, in that the filters also trap larger blood clots and other debris, and the filters tend to very quickly clog.

Rosenberg U.S. Pat. No. 3,765,536, issued on Oct. 16, 1973, proposes an improvement over the Swank filter, in that a cascade of filter elements is provided with increasing abilities for filtering smaller particles, such that the larger particles, e.g. debris, can be filtered by coarse prefilters, and the smaller particles, such as platelets and leucocytes, can be subsequently filtered from subsequent small pore filters. However, these filters are not only expensive to manufacture, but require very close tolerances, since any of the larger particles which pass through the prefilters will, ultimately, also clog the subsequent filters which are primarily used for filtering platelets and leucocytes. This problem is particularly accentuated, in that much of the debris and blood components are somewhat "plastic" in nature and can, therefore, "squeeze" through pores of sizes less than the ordinary size of those particles.

Marx U.S. Pat. No. 4,053,420, issued on Oct. 11, 1977, points to another problem which became apparent in regard to prior art filters, in that those filters, made of fine staple fibers sufficient to filter blood components, allowed some of the shorter, very fine, staple fibers to become separated from the filter and carried into the filtered blood. Those fine fibers cannot be subsequently separated from the filtered blood, since the fine fibers are of approximately the same size as some of the desired blood components in the filtered blood. The recognition that some of the fine fibers of the filter passed into the filtered blood, of course, caused considerable concern, since if those fine fibers lodge in the smaller blood vessels of, for example, the lungs, blockages of those small blood vessels can occur, with serious results. Marx, therefore, proposed making a filter out of a single monofilament, which was preferably crimped, and preferably star-shaped in cross section. When the single monofilament is stuffed into a convenience filter carrier, that monofilament cannot be displaced and enter into the filtered blood. However, as can be easily appreciated, this approach is open to considerable variation in filtration from filter to filter and, indeed, variations in filtration within a single filter, particularly near the sides of the filter carrier, since such stuffing of a monofilament cannot be uniformly achieved.

An effort to mitigate the above problem is disclosed in Kirsch, et al U.S. Pat. No. 4,132,650, issued Jan. 2, 1979, where that patent proposes avoiding fine fibers from passing through the filter and into the filtered blood by providing fibers with a lower melting range, such that the filter material may be heated, and the fibers of the filter may be essentially tackified together. While this approach is quite acceptable for avoiding fine fibers from passing through the filter, the filter described by that patent is, nonetheless, essentially the same as the prior art filters, in connection with the abilities to filter selected blood fractions or blood, especially leucocytes, and plugging due to debris, etc., as described above.

A somewhat similar approach is taken in Meyst, et al U.S. Pat. No. 4,157,976, issued on Jun. 12, 1979. In that patent, a stack of filter pads is joined at the periphery by heat sealing, to form an integral filter unit. The stacks of filter pads may be graduated in porosity, much in the manner described in the prior art, and as briefly noted above, and the fibers of the filters can be relatively long. This approach, however, while addressing the problem of long fibers stuffed into a carrier, so as to avoid channeling between stuffed long filaments and, especially, the walls of the filter carrier, does not solve the overall problem of variation in filtration.

Recently, a different approach has been taken in the art toward filtering leucocytes, and the basis of that approach is an adsorption phenomenon of the leucocytes on fibrous material. Pall, et al U.S. Pat. No. 4,880,548, issued on Nov. 14, 1989, describes fibers with a critical wetting surface tension for achieving adsorption of leucocytes, with that critical wetting surface tension being at least 90 dynes/cm. A similar approach is taken in Nishimura, et al U.S. Pat. No. 4,936,998, issued on Jun. 26, 1990, where fibers having nonionic hydrophilic groups and nitrogen-containing basic functional groups at the peripheral surface can selectively adhere leucocytes, as opposed to platelets.

More recently, the art has concentrated on the effects of fiber geometry for effective leucocyte filtration, and Watanabe, et al U.S. Pat. No. 4,701,2767, issued on Oct. 20, 1987, proposes a leucocyte filter of a non-woven fabric where the fibers of that fabric have an average diameter of from 0.3 microns to less than 3 microns, the fabric has a bulk density from 0.01 to 0.7 g/cm$^3$, and, most importantly, the average distance between any two of all of the adjacent fibers throughout the fabric is from 0.5 microns to 7 microns, as defined by the mathematical expression disclosed in that patent. With this geometry, it is said that improved leucocyte filtration takes place.

Finally, Nomura, U.S. Pat. No. 4,936,993, issued on Jun. 26, 1990, takes a somewhat similar approach in regard to fiber geometry and proposes a plurality of layers of staple, bleached Egyptian cotton with a bulk density of not less than 0.16 grams g/cm$^3$ and not more than 0.21 g/cm$^3$ on the blood inlet side of the filter, and not less than 0.21 g/cm$^3$ and not more than 0.23 g/cm$^3$ on the blood outlet side of the filter. The plurality of layers of fibers are packed in a range of 0.04 to 0.09 g/ml of the blood to be treated, and the layers on the blood inlet side of the filter must be in certain ratios to the layers on the blood outlet side of the filter.

From the foregoing, it can be seen that the art has long struggled with efforts in improving the filtration of blood fractions and whole blood, both from the standpoint of larger debris particles and from the standpoint of blood component filtration, including leucocyte filtration, and especially in regard to the latter. As can also be seen from the above, the art has taken many very different approaches to this perennial problem. As briefly noted above, those approaches vary from use of monofilaments to special fibers with special surfaces properties, to treating fibers to achieve special properties, to fiber geometry, and all of these approaches have certain advantages and disadvantages, again as very briefly noted above. However, in total, all of the prior art filters suffer from disadvantages. While one of the approaches may solve the problem of fine fibers entering into the filtered blood, those filters are not effective for leucocyte filtration which, ideally, should be above about 90%. On the other hand, some of the filters are effective for leucocyte filtration, but are difficult and expensive to manufacture and can introduce other foreign substances into the filtered blood, especially those with coated or treated fibers. Thus, the art has not provided a blood component filter, and especially a filter which will effectively remove leucocytes, that is satisfactory from all standpoints of filtration efficiency, safety and low-cost manufacture.

Accordingly, it would be a substantial advantage to the art to provide filters of the above nature where those disadvantages of the prior art filters are obviated. It would be of further benefit to the art to provide such filters which can be manufactured in a simple manner, and at a low cost, such that the filters are fully disposable, and, at the same time, ensure high effectiveness of filtration, especially of leucocytes.

BRIEF DESCRIPTION OF THE INVENTION

The present invention is based on several primary and several secondary discoveries. Firstly, as a primary discovery, it was found that in order for a filter to effectively deplete leucocytes from a blood fraction or whole blood passing therethrough, the depletion must be based on both the geometry of the fibers of the filter and the surface area of the fibers of the filter. In this regard, it was found that effective leucocyte filtration cannot be achieved by fiber geometry alone, and both geometry and surface area of the fibers of the filter material must be adequately provided in order to provide an effective leucocyte filter.

As a further primary discovery in this regard, it was found that the surface area of the filter material must be significantly greater than that of usual prior art commercial filters. Otherwise, the surface area of the filter for leucocyte filtration is simply not sufficient.

As a third primary discovery, it was found that since the depletion of leucocytes is a result of both fiber geometry and fiber surface area, effective leucocyte filters must have minimum depths in order to achieve the required fiber surface area of the filter material and to effectively deplete the leucocytes. Thus, while not appreciated by the prior art, the depth of the leucocyte filter is also important.

As a fourth primary discovery, it was found that an effective leucocyte filter must also have an overall bulk density, which reflects fiber geometry, sufficient to ensure a fiber geometry which will effectively play the required role of the fiber geometry in leucocyte depletion.

As a subsidiary discovery in the above regards, it was found that, in order to provide both increased surface area of the filter material and the necessary fiber geometry, the fibers of the filter material must have a relatively low and narrow average denier range, i.e. between about 0.05 and 0.75 denier. Those fibers, also, must have relatively short lengths, in order to achieve uniform processing in laying the fibers into a web. As a further subsidiary discovery, it was found that the fibers must have average lengths about 3 and 15 millimeters. Those fibers must also be disposed in the filter in a substantially uniform manner, such that those fibers form a matrix of fibers with spaces between adjacent interstices of the fibers when interlocked into a web.

As a very important primary discovery, it was found that ordinary textile fibers cannot produce the surface area of the fibers necessary for effective leucocyte depletion, since ordinary textile fibers can provide surface areas only in the order of up to about one square meter per gram, and that fiber surface area is too low for effective leucocyte depletion. Thus, as an important discovery, it was found that an effective leucocyte filter must have within the matrix of the textile fibers a significant amount of fibrillated particles of natural or synthetic polymeric materials, e.g. particles of a textile fiber material, where those fibrillated particles have a surface area of at least 5 and up to 60 square meters per gram. With the inclusion of these fibrillated particles in the matrix of the textile fibers, higher overall surface areas of the resulting filter material are achieved, and with this higher surface area, along with the fiber geometry, a very effective leucocyte filter may be provided, e.g. depletion rates of 99% or greater.

As a further discovery in this regard, it was found that the fibrillated particles must have a host of fine fibrils radiating from the particles such that those particles will interlock with the matrix fibers and such that the fibrillated particles are securely locked into the matrix of the fibers and cannot be displaced from that matrix during filtration of blood.

As a further discovery in this regard, it was found that the fibrillated particles must be in the matrix of the fibers in amounts such that the ratio of fibrillated particles to matrix fibers is between about 1:99 and 40:60.

Thus, broadly stated, the present invention provides a filter material for filtering leucocytes from a fraction of or whole human blood. The filter comprises a shape-sustaining laid textile web having a thickness of at least about 1, preferably 2, millimeter and a bulk density, as defined hereinafter, of between about 0.05 and 0.4 g/cm$^3$. There are a plurality of interlocked textile fibers with average deniers between about 0.05 and 0.75, average lengths between about 3 millimeters and 15 millimeters, and the textile fibers are substantially uniformly distributed in the web so as to form a matrix of the textile fibers with spaces between adjacent interstices of interlocked fibers.

A plurality of fibrillated particles of polymeric material, e.g. a textile fiber material, having a surface area of between 5 and 60 square meters per gram, are substantially disposed within the spaces of the matrix of the web. The fibrillated particles have a plurality of fine fibrils which are interlocked with adjacent textile fibers of the spaces, so as to dispose the fibrillated particles in the spaces and lock those fibrillated particles in those spaces, such that the fibrillated particles are not substantially displaceable from the web during filtration of blood or a blood fraction.

The ratio of the fibrillated particles to the textile fibers must be between about 1:99 and 40:60.

The invention also provides a method of filtering leucocytes from a fraction of or whole human blood comprising passing the blood through a filter material, as described above, and recovering the filtered blood.

DETAILED DESCRIPTION OF THE INVENTION

Figure 1:
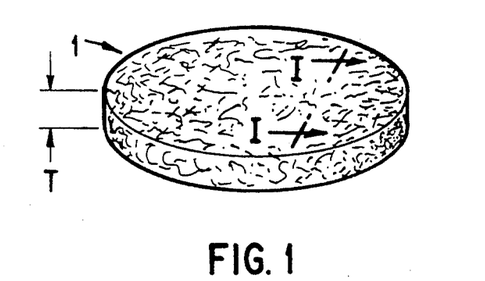
FIG. 1 is a perspective view of the filter made of the present material, in a configuration useful for placing in a filter carrier.

The present invention provides a filter material for filtering leucocytes from a fraction of or whole human blood. FIG. 1 shows such a filter made of such material. That filter, generally 1, is made from a filter material which is a shape-sustaining laid textile web. As shown in FIG. 1, the web has been cut in a circular configuration to form the filter and is suitable for loading into a cylindrical filter carrier. In this regard, the term "laid" is used in its ordinary technical sense. Thus, the web must be either air laid or wet laid, as opposed to, for example, needled, since it is in the laying process that the textile fibers and the fibrillated particles so interlock that the fibrillated particles are permanently bound into the filter material and will not be removed during filtration of blood. Needled textiles, for example, cannot provide such interlocking of the fibrillated particles with the textile fibers, and it is, therefore, necessary that the web be a laid web.

The thickness T of that web must be at least 1 millimeter, most preferably at least 2 millimeters, and may be up to about 30 millimeters, or more. Although these greater thicknesses can be used, the greater thicknesses do not provide appreciable further advantages of the invention and can decrease leucocyte depletion.

In this regard, it has been found that for effective leucocyte depletion from a blood fraction or whole blood passing through the filter, there must be sufficient depth of the filter that the leucocytes have an opportunity to be retained within the filter, both by the geometry of the matrix fibers and by the surface area of the matrix fibers and fibrillated particles, such that the depletion of the leucocytes is significant. In this regard, a 1 millimeter depth (1 millimeter thickness of the filter material) is considered to be the about the minimum effective depth, since, at this depth, about 70% of leucocytes will be depleted from the blood passing therethrough, and a 70% depletion is considered about the minimum depletion for effective filtration of leucocytes, although some depletion will occur with lesser depths.

However, if the depth of the filter is about 2 millimeters or more, then the depletion percentage of leucocytes increases to about 80% or more. When the depth of the filter is about 6 millimeters, the percentage of depletion of the leucocytes increases to about 99%. When the depth of the filter is about 8 millimeters, the depletion of the leucocytes is above 99%, but at about 8 millimeters, the pressure drop through the filler when filtering blood begins to significantly increase. That increase in pressure drop continues as the filter depth increases to about 10 millimeters, and at about 12 millimeters filter depth, the pressure drop becomes greater than that which would be desired for ordinary filtration of blood. It is for these reasons that the filter depth is usually between about 2 and 12 millimeters, although greater than 12 millimeters and up to about 30 millimeters may be used in special cases where the pressure drop is not of concern and depths of about 1 millimeter may be used where leucocyte filtration is not the primary concern. However, at above about 6 to 8 millimeters of depth, the depletion percentage of leucocytes does not substantially increase, and very little additional leucocyte depletion will be achieved at higher filter depths.

Depth is also important in regard to percentage of leucocyte depletion as a function of blood throughput. For example, if the thickness is too small, the filter may start with, for example, a 99% depletion for the first 200 mls of blood, but drop to 94% depletion for the next 200 mls of blood.

As will be explained in more detail below, the present web of filter material is preferably made on a conventional wet-laying machine. While such wet-laying machines can produce filter material of various thicknesses, as further explained below, it is both convenient and simple to control such conventional machines so as to produce web thicknesses of about 2 millimeters. Thus, to achieve greater filter depths, layers of the filter material (for example, 2 millimeter thickness per layer) are simply placed one upon the other to provide the desired filter depth.

The overall bulk density of the filter material must be between about 0.05 and 0.4 g/cm$^3$. As can be appreciated, the density of the filter material relates to the fiber geometry, and, as noted above, the fiber geometry plays an important role in both the depletion of leucocytes and in ensuring that the fibrillated particles are firmly and securely locked in the filter material. This density is the density of the laid and dried web, and does not include any fillers or the like and does not include any purposeful compression of the web other than as described below. At densities significantly below 0.05, the amount of matrix textile fibers in the filter material is simply not sufficient to ensure a large number of interstices between the matrix textile fibers for securely locking the fibrillated particles into the filter material. At a density above about 0.4, the amount of textile fibers to ensure such locking of the fibrillated particles has been exceeded, and the additional density simply results in increased pressure drop, without any significant further benefit to the filter material. Therefore, the density of the laid web must be between about 0.05 and 0.4 g/cm$^3$.

As can be easily appreciated, the density of a laid web of fibers depends on the method of measuring that density, since a thickness measurement must be made to calculate density and the thickness is open to interpretation. Ordinarily, with textile webs, the thickness is measured after a weight is placed on the web to provide a clear upper edge. This weight can vary with the particular filler material, and it is only necessary to have sufficient weight to provide a clear upper edge, but generally a weight of between about 0.5 to 1 lb. per square inch will provide such a clear upper edge.

Figure 2:
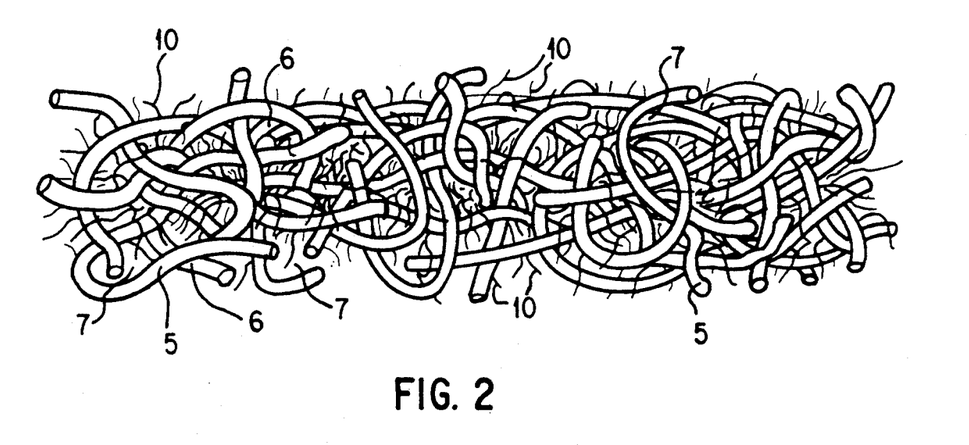
FIG. 2 is a highly diagrammatic partial cross-sectional view of a portion of the filter of FIG. 1, taken along lines I—I.

As seen in FIG. 2, which is a highly diagrammatic illustration of a portion of a section of the filter 1 of FIG. 1, the filter material is comprised of a plurality of matrix textile fibers 5, and these textile fibers have average deniers between about 0.05 and 0.75. As briefly noted above, it has been found that, in order to ensure a large number of interlocking interstices 6 between the textile fibers such that these interstices will securely lock the fibrillated particles into the filter material and to ensure as high a surface area as possible, the average denier must be low. In this regard, the present filter material provides high leucocyte depletion because the matrix fibers keep the fibrillated particles separated so that the high surface area thereof is not obscured or reduced due to coalescing or compacting. A controlling parameter in this regard is the matrix fiber length per unit weight, which for a given fiber material, e.g. polymeric material, is inversely proportional to denier. For example, with polyethylene terepthalate (PET), at 1.5 denier, the total length is 600,000 cm/gm, while at 0.1 denier the total length is 9,000,000 cm/gm. For purposes of the present invention, the total lengths should be between about 1,200,000 and 18,000,000 cm/gm, which for convenience, for most polymers of usual densities, is equivalent to about 0.05 to 0.75 denier. However, when a mixture of fibers of greatly different lengths is used, the denier will not be strictly equivalent to the length per unit weight. In such situations, instead of relying on the denier measurement, the length per unit weight should also be determined for each different fiber, and all of the matrix fibers must also have lengths between about 1,200,000 and 18,000,000 cm/gm, irrespective of the denier measurement. Nevertheless, since this is not the normal situation, for convenience in this specification and claims, denier is used, but it is with the expressed reservation and condition as specified above. This high length to weight provides a large number of interstices which provide points for the fibrillated particles to lock into the matrix fibers. It will also be appreciated that the above-noted average denier and average length of the fibers would result from a mixture of very low denier or short fibers and very high denier or long fibers, but this is not the intention, since this would not achieve the fiber geometry described above. Accordingly, while an acceptable average length and average denier can result from mixtures of fibers where some fibers have lengths less than 3 millimeters and deniers less than 0.05 and some have lengths greater than 15 millimeters and deniers greater than 0.75, to achieve acceptable fiber geometry, at least 60% of the fibers will have lengths and deniers within the above-noted ranges, preferably at least 70% and more preferably at least 80 to 85%. This prevents the release of both matrix fibers and fibrillated particles during filtration. Even as important, or perhaps more importantly, this provides fiber geometry of the matrix fibers which will keep the fibrillated particles separate, maintain the high surface area thereof and avoid clogging. It is for these reasons that the present high leucocyte depletion is obtained.

Thus, if the denier is significantly above 0.75, then the total length of total matrix textile fibers in the filter material is not sufficient in regard to the foregoing. On the other hand, if the denier is below about 0.05, the fibers become so fine that a relative dense packing of the fibers occurs in laying of those fibers in the laying process. This causes very small pore sizes in the matrix material which impedes passage of red cells and slows the flow rate during filtration.

Thus, it is necessary to ensure that the textile fibers are substantially uniformly distributed in the web, so that, correspondingly, the interstices are uniformly distributed and uniformly lock all of the fibrillated particles disposed throughout the filter material. In this regard, the matrix textile fibers must be so interlocked together that the fibrillated particles are, in turn, so interlocked to the textile fibers that the filter material can withstand a filtering blood pressure drop of at least two feet of head without substantial displacement of the fibrillated particles from the web. On the other hand, the pore size must not impede red cells or substantially reduce flow rate. All of this is ensured if the denier of the textile fiber is between about 0.05 and 0.75.

Also, if the denier is below about 0.05, the fibers become so fine that the pressure of filtration can cause the matrix textile fibers to compress. Such compression will cause the pore size between adjacent interstices to be so small that the filter material will quickly clog or channel during filtration. Thus, also, for this reason deniers below about 0.05 cannot be used.

Somewhat for the same reasons, the length of the textile fiber must be between about 3 millimeters and 15 millimeters. At lengths greater than about 15 millimeters, the intertwining and interlocking of the fibers during the laying process commences to diminish, and, consequently, the number of interstices formed between those textile fibers diminishes. This, in turn, reduces the number of positive points for interlocking of the fibrillated particles at the interstices of the fibers. On the other hand, if the fibers are less than about 3 millimeters, again, it is difficult to ensure an accurate laying of the textile fibers to further ensure that the textile fibers are uniformly distributed throughout the filter material, which, consequently, ensures uniform distribution of interstices for locking the fibrillated particles.

As can be seen in FIG. 2, the textile fibers are substantially uniformly distributed through the web so that as to form a matrix of the textile fibers. That matrix has spaces 7 between adjacent interstices 6 of the interlocked fibers. Within these spaces, there are a plurality of fibrillated particles 10 of very high surface area, including the surface area of the fibrils 11 of the fibrillated particles 10 (see FIG. 3). Those fibrillated particles 10 are disposed within spaces 7, as well as along and among the matrix textile fibers 5, so as to provide the high overall fiber surface area of the filter material. In this regard, fiber surface area refers to the area of the surface of all of the matrix textile fibers 5 and all of the fibrillated particles 10, including the fibrils 11 thereof, within the filter material. As noted above, it has been discovered that in order for the filter to be effective in depleting leucocytes, these fibrillated particles 10 must have a surface area of between 5 and 60 square meters per gram, and, as can be appreciated, this is an extremely high surface area.

As a bench mark, conventional filters, even with very fine textile fibers, may have a total surface area of all fibers of perhaps 0.5 square meters or even perhaps about up to one square meter per gram, although, usually, the total surface area will be much less. Even with non-textile fibers, such as meltblown fibers used in the above-noted patent to Watanabe, surface areas of only about one square meter per gram can be obtained. In contrast, the total surface area of all fibers and fibrillated particles in the present invention will be at least one and one-half times that surface area and more usually at least two to three or four or five times that surface area, e.g. a total surface area of at least about 1½ square meters per gram.

Figure 3:
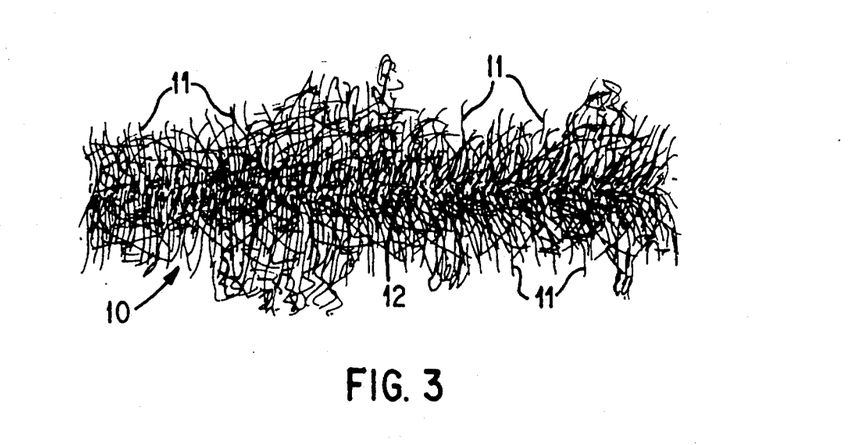
FIG. 3 is a highly diagrammatic illustration of a portion of the fibrillated particle of textile fiber material, used in the present invention.

As highly diagrammatically shown in FIG. 3, the fibrillated particles 10 have a plurality of fine fibrils 11 which extend and radiate from some generally elongated central portion 12 of the fibrillated particles 10. Those fibrils, as diagrammatically shown in FIG. 2, interlock among the matrix textile fibers 5 and particularly in the interstices 6 between matrix textile fibers. Thus, by wrapping the fibrils 11 around the matrix textile fibers 5 and by the fibrils 11 being interlocked between matrix textile fibers 5 at interstices 6 thereof, the fibrils 11 are securely interlocked with the matrix fibers 5 such that the fibrillated particles 10 are not substantially displaced from the filter material during filtration of blood.

While the fibrillated particles are described in more detail below, for purposes of explanation of FIGS. 2 and 3, a typical fibrillated particle is an elongated particle, as shown in FIG. 3 by the illustrated portion of a particle, with an elongated central proportion 12 and radiating fibrils 11. A length, width and depth of such a particle is, quite apparently, difficult to accurately measure or specify, but for understanding purposes, fibrillated particles have a general overall length of less than 1000 microns, e.g. 5 to 300 microns, but more usually somewhere about 5 to 50 microns. The width and depth vary considerably along the length of the central portion 12 and vary from 0.1 micron or below to 50 microns, but, generally, the widths and depths are between about 0.1 and 5 microns, and more usually between 0.2 and 0.7 micron.

From the above dimensions, it will be appreciated that a particular fibrillated particle 10, as shown in FIG. 2, can be so long that it actually weaves in and out of spaces 7 and one fibrillated particle may serpentinely lie in a number of spaces 7, e.g. up to 100 of such spaces 7. Thus, such a fibrillated particle, and especially the fibrils 11 thereof, has a multitude of interstices 6 with which to interlock and a large number of matrix fibers 5 about which serpentinely wrap. This makes a very secure deployment of the fibrillated particles and, thus, ensures that the fibrillated particles will not be displaced during normal filtration of blood or a blood component.

On the other hand, from the above dimensions, it will be appreciated that a particular fibrillated particle may essentially lie within a single space 7 bounded by adjacent interstices, with the fibrils 11 wrapped around adjacent matrix fibers and locked between adjacent matrix fibers forming adjacent interstices. Also, a particular fibrillated particle may be of any intermediate sizes between the two sizes discussed above, and combinations of such locking of the fibrillated particles will occur.

In all the above cases, it has been found that adequate locking of the fibrillated particles takes place and the particles are not substantially displaceable from the filter during filtration.

The weight ratio of the fibrillated particles to the textile fibers must be between about 1:99, and especially about 3:11, and about 40:60, especially about 20:80. If that ratio is less than about 3:97, the additional surface area supplied by the fibrillated particles is marginal for desired leucocyte filtration, and at below about 1:99, the surface area is simply not sufficient to achieve a minimum desired depletion of leucocytes, i.e. at least a 70% depletion. With increasing ratios of fibrillated particles to textile fibers, the depletion of leucocytes from blood will be correspondingly increased, such that at a ratio of about 5:95, the depletion percentage will be close to about 90%, and at about 10:90, the depletion will be about 99%. However, with increasing ratios, it will be appreciated that the number of matrix textile fibers, and the interstices formed thereby, will be correspondingly decreased, and there is not sufficient matrix fiber to keep the fibrillated material separated. Therefore, increasing the percentage of fibrillated particles results in lower average pore size and increased flow resistance without any increase in leucocyte depletion. At a ratio of about 40:60, the number of textile fibers in the filter material is decreased to the point where it is no longer reliable that most of the fibrillated particles will be separated, and it is for this reason that the ratio of fibrillated particles to textile fibers should not exceed about 40:60, particularly should not exceed about 30:70, especially 20:80. Further, at higher ratios, e.g. above about 6:94 or 10:90, it is preferred that additional provisions be made to ensure the permanent securing of the fibrillated particles in the filter material. These provisions include means for adhering the matrix fibers and the fibrillated particles to each other, e.g. heat tackifying adhesives, etc.

Figure 4:
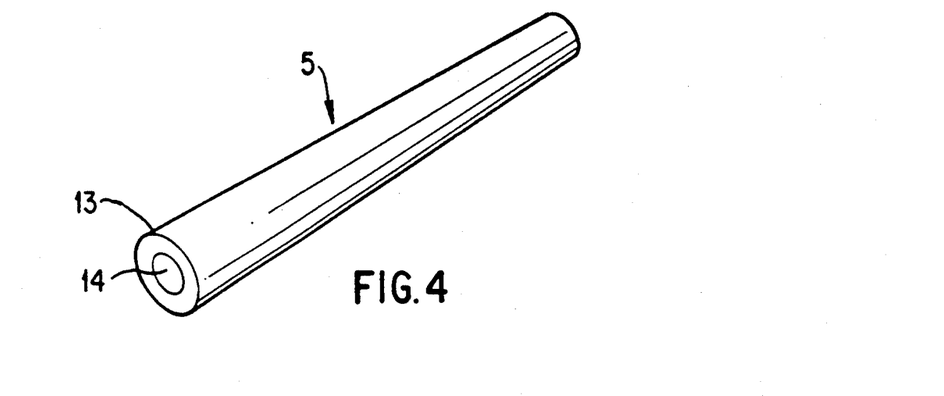
FIG. 4 is a perspective view of an alternate textile fiber useful in the present invention.

In this latter regard, as shown in FIG. 4, a portion of the matrix textile fibers 5 may have a sheath 13 and a core 14 with the deniers and lengths thereof being the same as described above. The sheath 13 will be of a low melt temperature polymer, and the core 14 will be of a higher melt temperature polymer. For example, the core 14 may be a polyester polymer, and the sheath 13 may be a low-melt olefin, such as polyethylene. When at least a portion of the matrix textile fibers of the filter material are the sheath/core fibers, the web of the filter material, when being processed, is subjected to temperatures such that the web has experienced temperatures sufficient to at least soften the polymer sheath 13 and cause at least some adherence of that softened sheath of the textile fibers 5 to each other and to, at least, part of the fibrils of the fibrillated particles. As can be appreciated, this will cause a bonding of the textile fibers together, to improve the strength of the interstices, and will cause bonding of the fibrils of the fibrillated particles to the sheath of the textile fibers. This will ensure better locking of the fibrillated particles in the filter material.

While as little as about 1% of the matrix textile fibers may have the sheath thereon, and at least some improvement will be provided for securing the fibrillated particles in the filter material, generally, at least about 5% of the matrix textile fibers should be the sheath/core fibers. On the other hand, while all of the textile fibers could be the sheath/core fibers, this would render the resulting filter material rather stiff, which is not desired, simply for convenience of handling, and, therefore, it is preferred that the sheath/core textile fibers be no greater than about 30%. At percentages of about 30% or less, there is no significant deterioration in the handling qualities of the filter material. Thus, a preferred range for the sheath/core textile fibers is between about 5% and 30%. Within this range, the filter material so locks the fibrillated particles into the filter material that the filter material can withstand a filtering blood pressure drop of at least five feet of head without substantial displacement of the fibrillated particles from the web.

The sheath fibers, if used, may be of a denier of the same range as the matrix fibers, i.e. 0.05 to 0.75 denier, but if 30% or less of sheath fibers are used, that denier may be higher, e.g. up to about 3 or 4 denier. For example, when about 10% sheath/core fibers are used, conventional 2 denier sheath/core fibers may be used.

The matrix textile fibers may be chosen from a wide range of conventional textile fiber materials, and may be chosen from, for example, one or more of polyester fibers, nylon fibers, olefin fibers, cellulosic fibers, natural fibers, synthetic fibers, inorganic fibers, glass fibers and ceramic fibers. However, it has been found that polyester fibers are particularly amenable to uniform laying, which provides uniform interstices, and are, therefore, preferred. The textile fibers may be crimped, if desired, to provide additional convolutions for additional interstices, although this is not required.

In the above regard, the term "textile fiber material" is used in its common sense, i.e. that the material, e.g. a polymer, is capable of being formed into a fiber which can be processed by conventional textile machines into a textile material, either woven or non-woven. This, of course, also means that the fibers of the "textile fiber material" must be capable of interlocking among themselves or with other fibers, i.e. a length sufficient that the fibers may be interlocked together to form a yarn or capable of matting to form a non-woven textile or engaged by barbs of needles for producing a needled textile. More usually, this will require a "staple" length of the fibers, i.e. one which allows the fibers to be twisted into a yarn.

The sheath fiber, if used, may have a core of the aforementioned textile fiber materials, and the sheath may be any low melting polymer. While a wide range of low melting polymer sheaths are known to the art, including methacrylates, vinyls and the like, polyolefin polymers, such as polyethylene or polypropylene, are preferred, since those polymers provide sheaths with very low melting points, and it is easy to soften those sheaths to provide the required adherence. The thickness of the sheath is essentially immaterial, since the only requirement of the sheath is that there be a sufficient layer of the sheath for adherence to adjacent fibers and fibrillated particles. Thus, the sheath can be from as little as 1% to 50%, e.g. 5 to 30% or 10 to 20% of the core diameter.

The fibrillated particles are particles of a synthetic or natural polymer, and a wide range of such polymers may be used, since it is not the particular polymer but the surface area thereof which is important. However, the polymers must be capable of substantial fibrillation, for the reasons expressed above. Thus, generally, the polymer will be a textile fiber material (polymer), since textile fiber materials, usually, are capable of being fi-brillated to a high degree. Any of the textile fiber materials noted above may be used as the fibrillated particles. In addition, the fibrillated particles may be of the same polymers as that of the sheath of the sheathed fiber, as noted above. However, it is preferred that the fibrillated particles be particles of the textile fiber materials of polyester fiber material, acrylic fiber material, nylon fiber material, polyolefin fiber material and cellulosic fiber material, since these materials easily fibrillate to high degrees and provide fibrillated particles with a multitude of fibrils, as described above. These materials also provide fibrils which easily attach to and lock with the matrix textile fibers, with or without sheath/core fibers. Further preferred is where the fibrillated particles are made of a textile fiber material which is predominantly a cellulosic fiber material, since fibrillated particles of that material provide a large number of fibrils, and it is especially preferred that the cellulosic fiber material be cellulose acetate, since a great number of fibrils are produced with that material, and the material has a natural hydrophilic nature and, thus, an affinity for leucocytes.

It is not necessary to describe in detail the fibrillated particles, since these fibrillated particles are known to the art and are commercially available. A full description of such fibrillated particles may be found in Keith, et al U.S. Pat. No. 4,274,914, issued on Jun. 23, 1981. That patent describes, in detail, the method of manufacture of the fibrillated particles and the fibrillated particles themselves. Those fibrillated particles have been used in the art as binders, primarily, especially in filter papers, and as especially used for binding adsorbents, such as activated carbon powders, in non-woven media. Among other applications are combustible shell casings, specialty papers, speaker cones, and substitutions for asbestos or aramid fibers in friction materials.

The aforementioned patent, the entire enclosure of which is incorporated herein by reference and relied upon for disclosure herein, also describes applications of the fibrillated particles to cigarette filters and face mask filters, where the fibrillated particles form those filters in combination with various fibers, particularly acetate and polyester fibers. Tobacco smoke filters are particularly described, and the use of the fibrillated particles in forming webs for cigarette-filter purposes is set forth in detail. Accordingly, while a detailed description of the fibrillated particles and the process for producing the present filters need not be set forth in this specification, a brief explanation is set forth below.

Thus, very briefly, those fibrillated particles have overall lengths of less than about 1000 microns and overall widths of about 0.1 to 50 microns, including the fibrils. They are three-dimensional particles, and the depth is approximately equal to the width. These particles are not fibers and cannot be spun into a yarn, i.e. not of staple length. They may be best diagrammatically visualized as extremely small duck "down", in the sense of their physical appearance as viewed through a microscope. The fibrils of the particles are extremely small, e.g. generally less than 0.01 micron in diameter and in the order of 1 to 50 microns long. The fibrils radiate from an elongated central portion, but not in any organized fashion.

Figure 5:
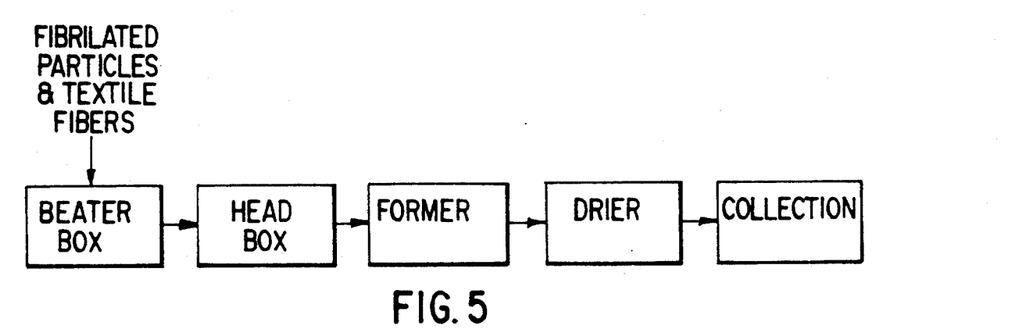
FIG. 5 is a block diagram of the overall process used for making the present filter material.

As shown in FIG. 5, the process, which is a known process and generally described in the above-noted patent, mixes the fibrillated particles and the textile fibers in a beater box to provide a furnish thereof. While the weight percent of fibrillated particles and fibers to the water in the beater box can vary widely, for most applications of fibrillated particles to be incorporated in the textile fibers, the total solids content (fibrillated particles and textile fibers) should be somewhere between about one and five percent. Sufficient mixing in the beater box is conducted until a homogenous slurry of the fibers and particles is obtained.

Thereafter, the furnish slurry is fed to a head box of an ordinary paper-making machine. Of course, if desired, intermediate stock tanks and mixers may be used, depending upon the particular machine and the schedule of processing thereon, all of which is well known in the art. Any of the conventional paper-making machines may be used, e.g. a rotating screen machine, a perforated drum machine, and the like, but a usual Fourdrinier machine is preferable, in view of the simplicity of operation of that machine and the control of the web thickness achieved thereby.

In any event, the furnish slurry of fibrillated particles and fibers is fed from the head box to the former of the machine, whether it be the rotating perforated drum or rotating screen or the Fourdrinier machine, and that slurry of fibers and particles is dewatered, usually by vacuum, to form a wet web.

That wet web is then passed to a drier, which is usually a series of steam-heated cans, and is heated sufficiently to dry the web. In the case of the use of sheath fibers, that drying temperature must be sufficient to ensure that the sheath of the sheath/core fibers is sufficiently softened to achieve the bonding, described above. That temperature, of course, will vary with the particular sheath, but, generally speaking, steam-heated cans with steam up to 1 to 2 atmospheres of superheat is more than sufficient to cause such adherence of the usual sheathed fibers. If a sheathed fiber is not used, then the steam-heated cans can be at almost any temperature, e.g. 120° F. to 300° F., consistent with drying the web to a relatively low moisture content, e.g. less than 10%, or usually less than 5% or 2% by weight moisture. From there, the dried web is collected in an ordinary collection mechanism, e.g. a roll collecting mechanism, and is then ready for cutting into desired filter shapes.

The foregoing is a conventional process and may be used to make the present filter material. However, it has been found that a modification of that process and the resulting filter material is of advantage. In this regard, it has been found that the fibrillated particles have a tendency to agglomerate during the process until the furnish slurry is deposited on the former. In the finished filter material, such agglomeration can cause undesired reduction in surface area and, correspondingly, decreased leucocyte depletion.

It has been found that such agglomeration can be avoided by incorporating into the furnish a small amount of small fibers. These small fibers are of less than staple size, i.e. non-staple fibers, and are used in amounts up to 10%. Amounts as low as 1%, however, are usually adequate. While these small fibers may be any natural or synthetic fibers, such as described above, small fibers are, preferably, ceramic and glass microfibers. These small fibers usually have average lengths of only about 10 microns or less and average diameters of about 0.1 to 2 microns.

It has also been surprisingly found that when mixed with the furnish, these small fibers are so interlocked with the fibrillated particles that they are not substantially displaceable from the filter material when filtering blood or a blood fraction.

As a means of avoiding any non-wetting and, hence, decreased filtration, in the filter material, the filter material may be treated with a small amount of an FDA approved wetting agent, which are known to the art, e.g. the Tweens surface active agents.

Figure 6:
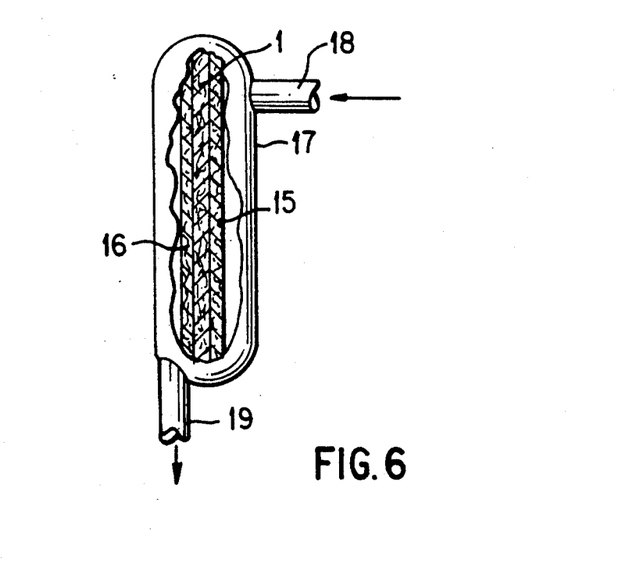
FIG. 6 is a diagrammatic view, partially in broken section, showing a useful, typical, completed filter arrangement, including the filter case.

The filter material may be formed into a filter device in any of the usual manners of the art, and FIG. 6 shows an acceptable example thereof. As shown in FIG. 6, the filter material 1 may be sandwiched between a prefilter 15 and a subsequent filter 16. The prefilter 15 is used to remove large agglomerates and the like which often occur in stored blood, and this prefilter can be any of the usual prefilters known in the art for that purpose. These prefilters can be woven or non-woven textile materials or metal meshes or the like, and the particular prefilter can be chosen as desired.

Similarly, the subsequent filter 16 may be simply a supporting subsequent filter, to give mechanical support to the present filter material and the prefilter. That subsequent filter may be, for example, a woven mesh or a wire mesh, simply to provide support for the pressure drop across the entire filter element (the prefilter, the present filter material and the subsequent filter). Here again, this subsequent filter can be as in the prior art, and no particular details are required in connection therewith.

The filter assembly is held in a conventional housing 17 which has a conventional inlet 18 and a conventional outlet 19. The filter assembly is held in that housing in any convenient manner for mechanically locking the filter element into the housing, e.g. mechanical clamps. Such housing, along with the filter elements therein, is desirably disposable, and with the low cost of the present filter material, such a filter assembly in such a housing is disposable at a low expense.

While FIG. 6 illustrates a convenient and conventional housing and arrangement of the filter elements, any of the other conventional housings and arrangements of filter elements known to the prior art may be used with the present filter material, since the present filter material is amenable to almost any desired configuration.

For certain filtering applications, it is desirable to choose among various properties of the filter material for achieving a desired end result. With the present filter material, choices of properties of filtration are easily obtained. Thus, for example, where the filtration is primarily intended to remove larger particles in the blood, with only a minimum depletion of leucocytes, then the filter material may have a relatively low ratio of fibrillated particles to textile fibers. On the other hand, where a high depletion of leucocytes is required, but the rate of throughput of the blood through the filter is not particularly critical, then a relatively high ratio of the fibrillated particles to textile fibers may be used.

Alternatively, such changes in surface area of the filter material may be achieved by choosing the surface area of the fibrillated particles. Thus, one could achieve such a filter material, as described above, by choosing fibrillated particles with a relatively low surface area, e.g. 10 square meters per gram, or, with the same ratio of fibrillated particles to textile materials, a filter material of high surface area could be achieved by choosing fibrillated particles with a relatively high surface area, e.g. 30 square meters per gram.

The preferred method of achieving different properties of the filter material is that of using fibrillated particles with a relatively high surface area, e.g. between about 10 and 30 or more square meters per gram, and adjusting the ratio of fibrillated particles to textile fibers.

Also, for the reasons explained above, some control over the properties of the filter material is achieved by the depth (thickness) of the filter material used in a filter application. In somewhat unusual circumstances, the depth (thickness) of the filter material may be as little as one millimeter, but as explained above, that depth will not provide desired depletion of leucocytes, e.g. at least a 70% depletion. There are cases, however, where only a smaller amount of leucocyte depletion is desired, and in those cases, the filter thickness may be as little as about one millimeter. Thus, by adjusting the thickness of the filter material, control is achieved over leucocyte depletion. On the other hand, where leucocyte depletion is of primary importance, and throughput is of little or no importance, the filter material may be as thick as 20 millimeters, while yet experiencing an acceptable pressure drop of the blood being filtered. However, as noted above, for most leucocyte filtration applications, the thickness should be between about 2 and 10 millimeters.

Somewhat similarly, the properties of filtration can be adjusted by the overall bulk density of the filter material (web) from which the filter is cut. While that bulk density should be between 0.05 and 0.4 g/cm$^3$, as described above, for a combination of maximum leucocyte depletion with maximum throughput of the filter, that bulk density should lie somewhere between about 0.08 and 0.2 g/cm$^3$. This is a very desirable filter configuration.

Also, somewhat similarly, the properties of the filter can be adjusted by the denier of the textile fibers. As noted above, the denier of the textile fibers should be between about 0.05 and 0.75, but with smaller deniers, greater surface area will be provided to the filter material, with greater leucocyte depletion, but greater pressure drop. On the other hand, with larger denier fibers, e.g. 0.75 denier, the surface area of the textile fibers will be decreased, but so will the pressure drop. A good combination between these two properties is where the denier is between about 0.1 and 0.6 denier, especially between 0.2 and 0.5.

Further, somewhat similarly, the properties of the filter can be adjusted by the length of the matrix textile fibers. While, as noted above, that length must be between about 3 and 15 millimeters, again, some effect on the filtration properties is achieved by choosing fiber lengths within that range. A good fiber length is between 5 and 10 millimeters, in that this length provides excellent interlocking, very uniform distribution of the laid web, and sufficient interstices for quite adequate binding of the fibrillated particles.

- While it is possible to change the properties of the filter material by any one or more of the above, most conveniently, those properties are adjusted simply by changing the ratio of the fibrillated particles to the textile fibers. This can easily be done in the common paper-making machine, and therefor is a most convenient means of adjusting the properties of the filter material, and is the preferred means of doing so. For example, when the fibrillated particles have a surface area of between about 10 and 30 square meters per gram, and the weight ratio of the fibrillated particles to the textile fibers, preferably polyester fibers, is between 5:95 and 15:85, a wide range of properties of the resulting filter can be achieved just within these parameters, and, therefore, that is a preferred method of adjusting the properties of the present filter material.

The invention will now be illustrated by the following examples, where all percentages and parts are by weight, unless otherwise noted, which is the case of the foregoing specification and claims.

EXAMPLE 1

Preparation of Prefilter 3 denier and 6 denier polyester fibers (Dacron Type 54) were carded on separate cards. The carded webs were crossed lapped separately onto a moving conveyor to form a mat with discrete layers of 3 and 6 denier fibers. The mat was needled with a conventional needle-punching machine. The needled mat was hot calendared (350° F.). The 3 denier side of the mat was glazed with a hot (500°-550° F.) knife. This material is Lydall style #CW140 which is a commercial filter material for use in a cardiometry reservoir.

Preparation of Filter Material

A wet laid non-woven was produced in the following manner: 85% Teijin 0.1 denier polyethylene terepthalate (PET) fibers of about 6 to 7 millimeters average length, 10% Chisso EKC 2 denier core (polypropylene)/sheath (polyolefin copolymer) fibers of about 5 to 9 millimeters average length and 5% Hoescht-Celanese cellulose acetate "fibrets" (fibrillated particles of textile fiber material) were weighed with adjustments made for the moisture content of the materials. About 33 grams of this furnish was placed in a commercial blender containing about 3 liters of water. The furnish slurry was blended at high speed for 2 minutes to achieve good dispersion. This slurry was added to a handsheet mold which was full of water. After addition, the furnish slurry was further dispersed by means of a paddle. Dewatering by gravity and vacuum resulted in the forming of a sheet on top of a papermaking wire which was at the bottom of the handsheet mold. Further dewatering was achieved by using vacuum. The sheet was dried at 250° F. on an Emerson speed dryer. The target weight for each sheet was 300 grams per square meter (gsm), and the thickness was approximately 2 mm.

Testing

For comparison purposes, also tested was a meltblown polyester material produced by Fiberweb North America. This is style #PPN-1023 which has a target weight of 100 grams per square meter and an average fiber diameter of 2.3 microns. This material is the filter material of a conventional filter and is recognized by the art as having superior leucocyte depleting properties.

The above materials were die cut into 3.9 inch circular pieces. One layer of the prefilter material was used with three layers of the present material for one set of tests. For comparison, one layer of prefilter material was used with six layers of the meltblown material. These materials had the following properties in the number of layers shown below to provide substantially the same weight of the present material and the meltblown material:

|  | Prefilter | Present Material | Meltblown |
|---|---|---|---|
| # of layers | 1 | 2 | 6 |
| Weight (gsm) | 470 | 600 | 600 |
| Thickness (mm) | 3.30 | 3.05 | 5.08 |
| Density (gm/cc) | .142 | .197 | .118 |

The filter media were inserted into the filter rigs of test filter assemblies. The filter media were oriented so that blood first passed through the Prefilter (6 denier side first) and subsequently through the Present Material or Meltblown. Fresh bovine blood (less than a day old) was supplied from a blood bag via tubing into the inlet of the filter rig. The supply blood was held at a constant height of about 24 inches to provide a constant head for gravity feeding of blood into the filter assembly. The filter rig was held so that the filter media was in a horizontal configuration, i.e. perpendicular to the flow of blood. Samples of blood were taken at both the inlet and outlet of the filter assembly after 200 and 400 ml of blood had passed through the filter assembly. The leucocyte content before and after filtration was counted using a standard Coulter counter. The results of the testing were as follows:

|  | % Leucocyte Depletion (200 mls) | % Leucocyte Depletion (400 mls) |
|---|---|---|
| Present Material | 98 | 94 |
| Meltblown | 42 | 33 |

As can be seen from the foregoing, on a comparable basis, the Present Material is more than twice as effective in leucocyte depletion as the conventional Meltblown filter material.

EXAMPLE 2

A prefilter similar to that of Example 1 was prepared, except that the prefilter had discrete layers of 1.5 and 3.0 denier PET fiber. This prefilter had a weight of about 7.4 ounces per square yard and a thickness of about 0.055 inch.

A needle-punched non-woven consisting of 100% 0.5 denier PET fiber was used as an intermediate filter. This material has a weight of 5.5 ounces per square yard and a thickness of 0.050 inch.

A Present Material was the same as Example 1.

Testing

For comparison, another wet laid non-woven Present Material was prepared which was the same as Example 1, except that the 5% cellulose acetate fibrillated textile material was not used and the 0.1 denier PET was increased from 85% to 90%.

Two filtration tests were conducted in the same manner as Example 1, except that the filter media configuration was changed. Test 1 used the prefilter material, the intermediate filter material and the Present Material with the 5% cellulose acetate fibrillated material. Test 2 was the same, except that the final filter did not have cellulose acetate fibrillated material. The prefilter was oriented so that the blood encountered the 3.0 denier side of the prefilter first and then the 1.5 denier side. The flow of blood then continued through the intermediate filter and the final filter.

The results of the tests were as follows:

Test 1: 84% reduction in leucocytes for 200 mls of fresh bovine blood processed.
Test 2: 34% reduction in leucocytes for 200 mls of fresh bovine blood processed.

From the above, it can be seen that the filter structure without the fibrillated particles is about equal to the effectiveness of a conventional filter material (see the results of Example 1), but with the present fibrillated material is more than twice as effective as the conventional filter material.

EXAMPLE 3

A prefilter was made according to Example 1, except that the prefilter had three discrete layers of 3, 1.5 and 0.5 denier, a total weight of 9 ounces per square yard and a thickness of 130 mls. This material was washed in a commercial washer to remove all contamination. Pluronic F68 surfactant was added to 500 mls of water, which was in turn added to the final rinse cycle of the wash process.

The same Present Material as Example 1 was immersed in a solution of 5 drops Tween 80 and 500 mls of distilled water then air dried. This material served as the final filter.

The prefilter and final filter were die cut to 2.5 inch circles.

Testing

For comparison, a Pall RC50 red cell/leucocyte filter (specially treated filter fibers) was disassembled and the filter media was retrieved.

For Test 1, the prefilter and final filter were inserted into the filter rig of Example 1, except the rig was down scaled to accommodate a 2.5 inch filter media. Test 2 was the same, except the Pall media was used. In both tests, the filter media was oriented so blood first encountered the prefilter (3.0 denier side first) then the final filter.

The results of the tests were as follows:
Test 1: 200 mls of bovine blood, 94% leucocyte depletion 400 mls of bovine blood, 43% leucocyte depletion
Test 2: 200 mls of bovine blood, 89% leucocyte depletion 400 mls of bovine blood, 30% leucocyte depletion As can be seen, the present filter material is significantly better than even filter material made of the expensive specially treated fiber of the newest blood filters.

EXAMPLE 4

The prefilter described in Example 3 was used in this example.

A Present Material similar to Example 1 was prepared, except that the furnish was 70% 0.5 denier PET, 10% core/sheath fibers, 10% cellulose acetate fibrillated material and 10% code 106 microglass fiber made by Manville.

The filter materials were die cut to 2.574 inch circles.

Testing

These were inserted into a test filter rig, as described above. The filter media was oriented in the vertical direction and the blood entered at the bottom of the filter media and exited at the top. The media was oriented so that blood first encountered the prefilter material (3.0 denier side first).

The rig was connected with tubing to a unit of human packed red cells about 10 days old. 80 gms of packed cells were passed through the filter. The leucocyte level of the filtered cells was reduced by more than 99%.

What is claimed is:

1. A filter material for filtering leucocytes from a fraction of or whole blood, comprising:
   (A) a shape-sustaining laid textile web having a thickness of at least about 1 millimeter and a bulk density of between about 0.05 and 0.4 g/cm³, said web having:
      (i) a plurality of interlocked, textile fibers with average deniers between about 0.05 and 0.75 and average lengths between about 3 millimeters and 15 millimeters, said textile fibers being substantially uniformly distributed in said web so as to form a matrix of the textile fibers with spaces between adjacent interstices of interlocked fibers;
      (ii) a plurality of fibrillated particles of polymeric material having a surface area of between about 5 and 60 square meters per gram substantially disposed within said spaces of the matrix, said fibrillated particles having a plurality of fine fibrils which are interlocked with adjacent textile fibers of said spaces such that the fibrillated particles are not substantially displaceable from said web during filtration of said blood; and
   wherein the weight ratio of the fibrillated particles to the textile fibers is between about 1:99 and 40:60.

2. The filter material of claim 1 wherein the textile fibers are so interlocked together and the fibrillated particles are so interlocked to the textile fibers that said filter material can withstand a filtering blood pressure drop of at least 2 feet of head without substantial displacement of the fibrillated particles from the web.

3. The filter material of claim 2 wherein at least a portion of the textile fibers have a sheath of low melt temperature polymer thereon and the web has experienced a temperature sufficient to at least soften said polymer and cause at least some adherence of the textile fibers to other textile fibers and to the fibrils of the fibrillated particles.

4. The filter material of claim 3 wherein the sheath is made of a polyolefin polymer.

5. The filter material of claim 3 wherein from about 1% to about 30% of the textile fibers have said sheath thereon.

6. The filter material of claim 5 wherein from about 5% to about 30% of the textile fibers have said sheath thereon and the filter material can withstand a filtering blood pressure drop of at least 5 feet of head without substantial displacement of the fibrillated particles from the web.

7. The filter material of claim 5 wherein from about 5% to 30% of the textile fibers have a sheath thereon.

8. The filter material of claim 7 wherein the denier of the textile fibers have a sheath thereon is up to about 4 denier.

9. The filter material of claim 3 wherein the sheath is of a low-melting polymer and the core is of a high-melting polymer.

10. The filter material of claim 9 wherein the low-melting polymer is selected from the group consisting of methacrylates, vinyls and polyolefins.

11. The filter material of claim 1 wherein the textile fibers are one or more of polyester fibers, nylon fibers, olefin fibers, cellulosic fibers, natural fibers, synthetic fibers, inorganic fibers, glass fibers and ceramic fibers.

12. The filter material of claim 11 wherein the textile fibers are predominantly polyester fibers.

13. The filter material of claim 1 wherein the fibrillated particles are particles of a textile fiber materials selected from the group consisting of polyester fiber material, acrylic textile material, nylon fiber material, polyolefin fiber material and cellulosic fiber material.

14. The filter material of claim 13 wherein the textile fiber material of the fibrillated particles is predominantly cellulosic fiber material.

15. The filter material of claim 14 wherein the cellulosic fiber material is cellulose acetate.

16. The filter material of claim 1 wherein the fibrillated particles have lengths of less than about 1000 microns and widths of about 0.1 to 50 microns.

17. The filter material of claim 16 wherein the fibrillated particles have lengths of 5 to 300 microns.

18. The filter material of claim 16 wherein the fibrillated particles have lengths of 5 to 50 microns.

19. The filter material of claim 16 wherein the fibrillated particles have widths of about 0.1 to 5 microns.

20. The filter material of claim 16 wherein the fibrillated particles have widths of about 0.2 to 0.7 microns.

21. The filter material of claim 1 wherein the fibrillated particles have lengths of about 5 to 50 microns, widths of about 0.1 to 5 microns and a surface area of between about 5 and 30 square meters per gram.

22. The filter material of claim 21 wherein said surface area of the fibrillated particles is at least 10 square meters per gram and up to 60 square meters per gram and the surface area of the filter material is at least 1.5 square meters per gram.

23. The filter material of claim 1 wherein the web thickness is between about 1 millimeter and 10 millimeters.

24. The filter material of claim 1 wherein the web bulk density is between about 0.08 and 0.2 g/cm³.

25. The filter material of claim 1 wherein the denier of the textile fibers is between about 0.1 and 0.6.

26. The filter material of claim 1 wherein the average denier of the textile fibers is between about 0.2 and 0.5, the average length is between about 5 and 10 millimeters and the textile fibers are polyester textile fibers.

27. The filter material of claim 1 wherein the fibrillated particles have a surface area of between about 10 and 30 square meters per gram, the textile fibers are polyester fibers and the weight ratio of fibrillated particles to polyester fibers is between about 3:95 and 15:85.

28. The filter material of claim 1 wherein 1 to 10% of small non-staple fibers are contained in the web.

29. The filter material of claim 28 wherein the small non-staple fibers are ceramic or glass fibers.

30. The filter material of claim 29 wherein the small non-stable fibers have average lengths of about 10 microns or less and average diameters of about 0.1 to 2 microns.

31. The filter material of claim 1 having a surface active agent thereon.

32. The filter material of claim 1 wherein the web thickness if between about 1 millimeter and 30 millimeters.

33. The filter material of claim 1 wherein the web thickness is between about 2 millimeters and 30 millimeters.

34. The filter material of claim 33 wherein the web thickness is up to 12 millimeters.

35. The filter material of claim 33 wherein the web thickness is up to 8 millimeters.

36. The filter material of claim 33 wherein the web thickness is up to 6 millimeters.

37. The filter material of claim 1 wherein at least 60% of the textile fibers have the said lengths and deniers.

38. The filter material of claim 1 wherein at least 70% of the textile fibers have the said lengths and deniers.

39. The filter material of claim 1 wherein at least 80% of the textile fibers have the said lengths and deniers.

40. The filter material of claim 1 wherein said weight ratio of particles to fibers is between about 3:97 and about 40:60.

41. The filter material of claim 1 wherein said weight ratio of particles to fibers is between about 3:97 and about 20:80.

42. The filter material of claim 1 wherein the matrix fibers and fibrillated particles are adhered to each other.

43. The filter material of claim 42 wherein the matrix fibers and fibrillated particles are adhered to each other with an adhesive.

44. A method for filtering leucocytes from a fraction of or whole human blood, comprising passing said blood through the filter material of claim 1 and recovering the filtered blood.

* * * * *

UNITED STATES PATENT AND TRADEMARK OFFICE
CERTIFICATE OF CORRECTION

PATENT NO. : 5,190,657
DATED      : March 2, 1993
INVENTOR(S): David G. HEAGLE and John J. HIERS It is certified that error appears in the above-identified patent and that said Letters Patent is hereby corrected as shown below:

Column 19, line 59 (claim 8, line 2 thereof), change "have" to --having--.

Column 20, line 6 (claim 13, line 2 thereof), change "materials" to --material--.

Column 20, line 56 (claim 30, line 2 thereof), change "non-stable" to --non-staple--.

Column 20, line 62 (claim 32, line 2 thereof), change "if" to --is--.

Signed and Sealed this

Fourteenth Day of November, 1995

Attest:

BRUCE LEHMAN

*Attesting Officer*     *Commissioner of Patents and Trademarks*